United States Patent [19]

Kosugi et al.

[11] Patent Number: 5,010,004

[45] Date of Patent: Apr. 23, 1991

[54] METHOD FOR CONTINUOUS REACTION WITH FLUIDIZED IMMOBILIZED LIPASE

[75] Inventors: Yoshitsugu Kosugi; Hideoki Tanaka, both of Tsukuba; Hideo Suzuki, Tokyo; Masaru Shiraki, Tsukuba, all of Japan

[73] Assignees: Agency of Industrial Science & Technology; Ministry of International Trade & Industry, both of Tokyo, Japan

[21] Appl. No.: 255,599

[22] Filed: Oct. 11, 1988

[30] Foreign Application Priority Data

Oct. 9, 1987 [JP] Japan ................. 62-255057

[51] Int. Cl.$^5$ .................. C12P 7/64; C12N 11/08; C12N 9/20; C12M 1/40
[52] U.S. Cl. ............................. 435/134; 435/177; 435/180; 435/182; 435/198; 435/288; 435/813
[58] Field of Search ............... 435/134, 174, 177, 180, 435/181, 182, 288, 813, 198

[56] References Cited

FOREIGN PATENT DOCUMENTS 61-85195  4/1986  Japan .
63-59896  3/1988  Japan .

OTHER PUBLICATIONS

Kimura, et al., *Eur. J. Appl. Microbiol. Biotechnol.,* 17:107–112 (1983).

Lieberman, et al., *Biotechnology and Bioengineering,* 17:1401–1419 (1975).

*Extract Engineering,* Hirata et al., pp. 166–167 (1964).

*Primary Examiner*—David M. Naff
*Attorney, Agent, or Firm*—Oblon, Spivak, McClelland, Maier & Neustadt

[57] ABSTRACT

A water-soluble substrate and an oily substrate are continuously reacted with immobilized lipase in a reaction vessel having vertically maintained apart upper and lower conically-shaped regions, respectively, for separation of a water-soluble product and an oily product, a plurality of lipase reaction zones each containing immobilized lipase capable of being fluidized and an agitating means, and a plurality of intermediate separation zones for separation of an oily substance and a water-soluble substance. The lipase reaction zones and the intermediate separation zones are disposed alternately between the upper and lower conically-shaped separation regions. Boundaries between the lipase reaction zones and intermediate separation zones are pervious to liquid but impervious to the immobilized lipase. The water-soluble substrate and oily substrate are passed in counterflow contact through the lipase reaction zones and intermediate separation zones and mutually contact the immobilized lipase which has been fluidized. An oily product is recovered from the upper conically-shaped separation region and a water-soluble product is recovered from the lower conically-shaped separation region.

13 Claims, 1 Drawing Sheet

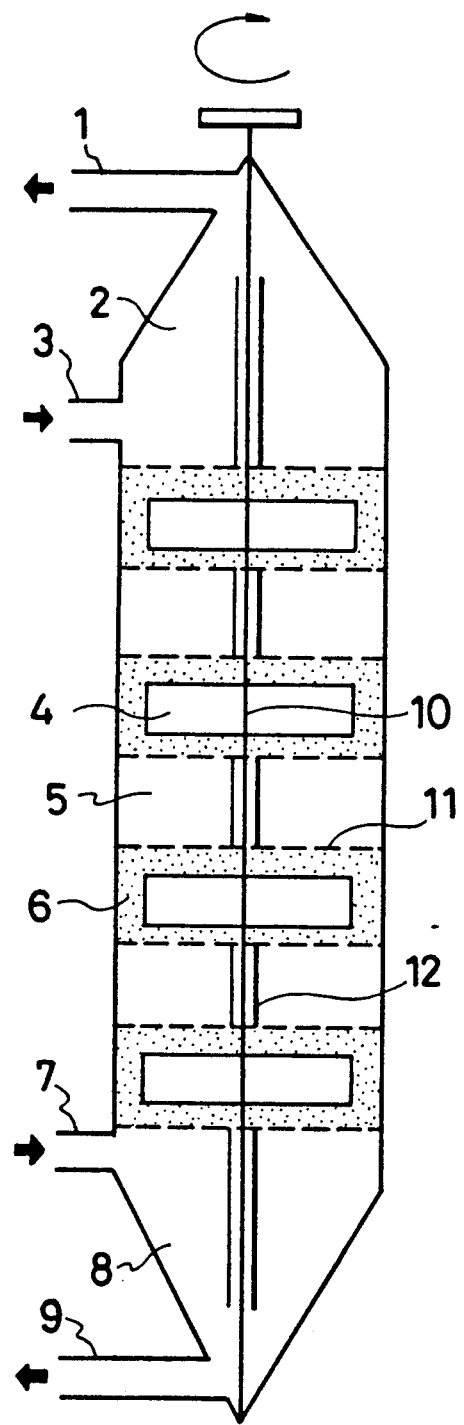

METHOD FOR CONTINUOUS REACTION WITH FLUIDIZED IMMOBILIZED LIPASE

BACKGROUND OF THE INVENTION

1. Field of the Invention

In the reaction by the use of an immobilized lipase, such heterogeneous substrates as an oily substrate and a water-soluble substrate are caused by mass transfer to reach a lipase held fast in a particulate immobilizing carrier, undergo transformation into heterogeneous products, i.e. an oily product and a water-soluble product, by the lipase, and depart from the lipase again by mass transfer. This invention is directed to a method for performing the reaction advantageously by enabling the mass transfer of the continuous-phase substrates to proceed efficiently and continuously.

The lipase is an enzyme which acts upon ester bonds and, as such, finds utility in such reactions as ester hydrolysis, ester synthesis, and transesterification. It is also utilized for the optical resolution of racemic esters, acids, and alcohols. Thus, the lipase is expected to find extensive utility in various applications in the oil and fat industry, the pharmaceutical industry, and the foodstuff industry, for example.

2. Prior Art Statement

A method which, by the use of a column packed with a photolinkable gel entrapping an immobilized lipase, carries out the reaction by preparatorily mixing water and an oil by stirring and circulating the resultant oil-water mixture in the form of emulsion to the column has been known to the art [Y. Kimura et al., Eur. J. Appl. Microl. Biotechnol., 17, 107 (1983)]. Besides, a method which, by the use of an immobilized lipase column developed earlier by the inventors, carries out the reaction by continuously feeding into the column a water-soluble substrate via a middle upper stage and an oily substrate via a middle lower stage respectively and collecting continuously an oil product through the upper end of the column and a water-soluble product through the lower end thereof (Kosugi et al.; U.S. Pat. application Ser. No. 586,563, dated Mar. 6, 1984, now abandoned) and a method which, by the use of a multistage reaction vessel, effects the reaction by alternately repeating separation and mixture of an immobilized lipase, an oily substrate, and a water-soluble substrate thereby bringing the oily substrate and the water-soluble substrate into counterflow contact with the immobilized lipase (Kosugi et al.; Japanese Patent Public Disclosure SHO 63(1988)-59896) have been known to the art.

The known method which involves the circulation of a preparatorily emulsified mixture to the immobilized lipase column cannot be easily carried out in the form of a continuous operation because the emulsion particles are diffused inside the immobilizing carrier at a notably low speed and, therefore, the reaction solution must be circulated to the immobilized lipase column time and again. Moreover, this method is incapable of separately collecting the oily product and the water-soluble product continuously.

The method which involves the counterflow supply of the oily substrate and the water-soluble substrate to the immobilized lipase column is required to secure a flow path adapted for the oily substrate and the water-soluble substrate to be advanced as preparatorily mixed with each other so as to preclude the phenomenon of channeling, i.e. complete separation of the flow path of the oily substrate from that of the water-soluble substrate inside the column, and also is required to operate the column in such a manner that the feed rate of the substrates will be lower than the speed of separation between the water and the oil inside the column. Thus, this method is subject to numerous operational restrictions and, therefore, cannot easily make full use of the activity of the immobilized lipase.

The method which, by the use of the multistage reaction vessel, effects the reaction by alternately repeating separation and mixing of the immobilized lipase, the oily substrate, and the water-soluble substrate thereby bringing the oily substrate and the water-soluble substrate into counterflow contact with the immobilized lipase primarily consists in a batchwise operation of the multistage reaction vessel. For this method to produce a continuos reaction and permit continuous collection of the oily product and the the water-soluble product, therefore, the reaction vessel requires a complicated piping system and the operation of this piping system requires a complicated control. Further, the mixing of the three components inevitably entails formation of a fine emulsion, rendering it difficult to separate the oil from the water. If the separation and the mixing were carried out in two separate reaction vessels to preclude the difficulty of the separation, the operation would necessitate a separation time in addition to the reaction time and could hardly be called an efficient method.

The inventors have already developed an immobilized lipase capable of retaining the activity thereof even in the presence of a higher fatty acid and have demonstrated that this immobilized lipase permits continuous protracted use (U.S. Pat. application Ser. No. 586,563, dated Mar. 6, 1984). Since this immobilized lipase uses as its carrier an ion exchanger specifically developed with a view to lowering the head loss of the liquid inside the column. Thus, this immobilized lipase is not suitable for the fluidized bed to be used in the method of the present invention.

As an example of the immobilized lipase used in the form of a fluidized bed, the use of a lipase immobilized in stainless steel beads of a large specific gravity has been reported. In the reported experiment, hydrolysis of a tributyrin emulsion is carried out in a fluidized bed reactor keeping the immobilized lipase in a floating state therein [R. B. Liberman et al.; biotechnol. Bioeng., 17, 1401 (1975)].

The above mentioned method causes the emulsion of substrates to flow up and circulate through a mass of fine beads of immobilized lipase having a large specific gravity. It is, therefore, not free from the influence of the resistance offered to the diffusion of the emulsion particles inside the carrier, is incapable of producing a perfect continuous reaction, and is unable to effect separate collection of the oily product and the water-soluble product. If the immobilized lipase of a large specific gravity is used in the method of the present invention, the possibility ensues that the immobilized lipase will be discharged in conjunction with the water-soluble product of a large specific gravity.

OBJECT AND SUMMARY OF THE INVENTION

The inventors have perfected this invention after continuing a study directed to the elimination of the drawbacks standing on the way of realizing practical use of the prior techniques mentioned above.

To be specific, this invention is directed to a method for continuous reaction of a water-soluble substrate and an oily substrate in the presence of an immobilized lipase kept in the form of a fluidized bed, which method comprises providing an upper and a lower separation region respectively for separation of a water soluble substance and an oily substance vertically kept apart from each other, lipase reaction zones each containing the immobilized lipase in the fluidized state and incorporating therein agitating means and zones for the separation of an oily substance and a water soluble substance alternately disposed between the upper and lower separation regions, feeding the water-soluble substrate into the upper part of the uppermost lipase reaction zone and the oily substrate into the lower part of the lowermost lipase reaction zone, causing the immobilized lipase to fluidize and to come into mutual counterflow contact with the oily substrate and the water-soluble substrate in the lipase zone and recovering the oily product containing liquid from the upper part of the separation region and recovering the water-soluble product-containing liquid from the lower part of the lower separation region.

In accordance with the method of this invention, the reaction of the substrates by the immobilized lipase and the separation of the oily product and the water-soluble product of the reaction are continuously carried out. Specifically, the substrates each in the form of a continuous phase are supplied under agitation and consequently caused to undergo the reaction and give rise to an emulsion in the form of a discrete phase. This emulsion renders difficult the separation of the oil and the water. The present invention solves the problem due to the emulsion by providing reaction zones and zones for the oil-water separation which are vertically connected. Moreover, the method of the present invention permits continuous enzymatic reaction and continuous separate collection of the oily product and the water-soluble product of the reaction. Actually there are times when the oily product and the water-soluble product which are collected after the enzymatic reaction possibly contain respective unaltered substrates.

By supplying the oily substrate at a feed rate higher than the feed rate at which the water-soluble substrate is supplied, continuous concentration of the water-soluble product can be realized. Optionally, the products (possibly containing respective unaltered substrates) of the enzymatic reaction may be partly used as the substrates for supply to the reaction zone. By using the water-soluble product repetitively as a feed substrate at a high rate, for example, it is made possible to diminish the resistance offered to the external diffusion during the approach of the substrate to the carrier and effect the reaction with enhanced efficiency. When the water-soluble product is circulated as a feed substrate, since it is not acquired as a product, continuous manufacture of this product is no longer attained. The production in this case, therefore, is attained continually. By lengthening the time of this circulation, it becomes possible to attain concentration of the water-soluble product of the reaction.

The inventors have continued a study in search of a process for producing an immobilized lipase suitable for use in the method of this invention. It has been consequently ascertained to them that an immobilized lipase produced by causing a fine hydrophobic carrier possessing particle diameters in the range of 0.02 mm to 0.3 mm to immobilize therein a lipase and allowing an anion exchange residue binding no lipase molecule to be deposited on the surface of the carrier is highly effective in carrying out the enzymatic reaction. For the method of the present invention, it is necessary to dispose in each of the boundaries between the alternating lipase reaction zones and zones for the separation of the oily substance and the water soluble substance a mechanism such as, for example, a sieve which is pervious to a liquid substance and impervious to the immobilized lipase. When the particulate carrier has particle diameters exceeding 0.02 mm, the possibility of the carrier passing through the sieve need not be taken into consideration. Moreover, the immobilized lipase is both hydrophilic and hydrophobic and, on gradual adsorption of water or oil, is caused to vary in specific gravity. Thus, it serves the purpose of immobilized lipase from flowing out of the reaction system. When the particulate carrier has particle diameters not exceeding 0.3 mm, though it is liable to adhere to the reaction vessel and gather into coarse particles, it improves mass transfer of heterogenous substrates. The immobilized lipase thus obtained has high lipase activity, because of the high ratio of immobilization and performs the enzymatic reaction with high efficiency.

The above and other objects and features of the invention will become more apparent from the following detailed description with reference to the accompanying drawing.

BRIEF DESCRIPTION OF THE DRAWING

The drawing illustrates a typical apparatus for working the present invention.

DETAILED DESCRIPTION OF THE PREFERRED EMBODIMENTS

Now, the present invention will be described more specifically below with reference to the accompanying drawing illustrating a typical apparatus for working the present invention. In the diagram, reference numeral 1 stands for an outlet for an oily product-containing liquid, 2 for an upper separation region, 3 for an inlet for feeding a water-soluble substrate, 4 for a agitating blade, 5 for a separation zone, 6 for a lipase reaction zone, 7 for an inlet for feeding an oily substrate, 8 for a lower separation region, 9 for an outlet for a watersoluble product-containing liquid, 10 for a agitating shaft, 11 for a sieve plate disposed in the boundary between a lipase reaction zone and a dispersion zone, and 12 for a agitating shaft cover.

The upper separation region 2 and the lower separation region 8 are each desired to be in a conical shape. The conical shape is desirable because the fine emulsion possibly formed during the mixing of the two substrates is allowed to collide against the wall of the separation region before said fine emulsion reaches the outlet 1 for the oily product-containing liquid or the outlet 9 for the water-soluble product-containing liquid and break into a continuous phase before the emulsion in the form of discrete phase reaches the outlet, so that the separation of the oily phase from the aqueous phase is attained with enhanced ease. When the reaction solution is of such nature as to permit no easy separation of the oily phase from the aqueous phase or when the fine water particle suspended in the oily phase is subject to a protracted operation, the water particles may possibly be condensed and accumulated in the form of water drops in the transfer path for the oily product. When the separation regions mentioned above are provided each with a portion packed with glass beads for example, the fine emulsion in the form of discrete phase is broken into a continuous substance so thoroughly that the separation of the oily phase from the aqueous phase is accomplished substantially perfectly. For the efficiency of the separation of the water and the oil, the portion of stirring shaft is desired to be provided with the agitating shaft cover 12 and consequently prevented from the influence of the shaft. The upper separation region 2 is provided in the upper part thereof with the outlet 1 for the oily product-containing liquid and in the lower part thereof with the inlet 3 for feeding the water-soluble substrate. The lower separation region 8 is provided in the lower part thereof with the outlet 9 for the water-soluble product-containing liquid and in the upper part thereof with the inlet 7 for feeding the oily substrate. As described above, the separation regions are each disposed between the inlet for the substrate and the outlet for the product. Owing to this particular setup, the substrate is prevented from being entrained by the product. The separation zones and the separation regions are desirably kept at a temperature exceeding 50° C., because this temperature is proper for the separation of the oily phase from the aqueous phase and also is effective in preventing the relevant portions of the reaction vessel from pollution with infections microbes. They are desired to be provided as with a jacket so as to be maintained at the temperature above 50° C.

For this invention, a cylindrical reaction vessel can be used which is provided with agitating means in each of the lipase reaction zones. In this reaction vessel, there is placed the immobilized lipase. The agitating means is desired to be an angled paddle shaft of large size capable of producing a gentle agitating motion such as to decrease the possible physical breakage of the immobilized lipase. It is further desired to be capable of stirring the interior of the reaction vessel in the direction of inducing floatation of the immobilized lipase. The lipase reaction zones are adapted so as to be kept at a prescribed temperature. The sieve plates 11 which separate the separation zones 5 and the lipase reaction zones 6 are desired each to be something like a stainless steel sieve plate containing meshes so small as to preclude passage of the immobilized lipase. There is the possibility that the bubbles adhering to the immobilizing carrier will gather into large masses beneath the sieve plates 11 at the outset of the reaction and interfere with smooth progress of the separation of the oily phase from the aqueous phase in the reaction vessel. To preclude the trouble, the bubbles must be withdrawn by physical stimulation or by the use of deaeration means which is installed exclusively for this purpose.

As the separation zones 5 to be formed in the middle stage of the apparatus for working this invention, there can be generally used tubular enclosures having height enough to permit effective separation of the oil and the water. If these enclosures have an unduly large height, the oil-water separation consumes much time and the apparatus as a whole assumes a large inner volume. The separation zones, therefore, are desired to have as small a height as permissible In order for the water-oil separation to proceed smoothly, the agitating shaft part is desired to be provided with the agitating shaft cover 12 adapted to prevent the stirring shaft from the influence of the shaft. The fact that the apparatus is provided with a plurality of a lipase reaction zone 6 and a separation zone 5 is effective in curbing the occurrence of fine emulsion in consequence of protracted agitating of the heterogeneous substrates.

The term "oily substrate" as used in this invention refers to a substrate for the reaction to be caused by the immobilized lipase. As examples of the substrate, such substances as oils and fats, waxes, phospholipids, various esters, monoglycerides, diglycerides, and fatty acids which are hardly soluble in water may be mentioned. The substrate has a smaller specific gravity than water and is soluble in such nonpolar solvents as isooctane, hexane, and heptane. In conjunction with the oily product, this oily substrate forms an oily phase. The substrate which incorporates therein the aforementioned nonpolar solvent for the purpose of facilitating the oil-water separation or solubilizing the substrates is also included as an oily substrate. The term "water-soluble substrate" as used herein refers to water, a water-soluble organic substance such as glycerin, glycerophosphoric acid, or an aqueous solution of the organic substance. In conjunction with the water-soluble product, this water-soluble substrate forms an aqueous phase.

The lipase to be used for this invention is an enzyme produced by microorganisms or higher animals or plants. It is a biochemical macromolecular compound which acts on ester bonds and induces ester resolution, transesterification, or ester synthesis. The substances which exhibit this activity and are called esterases or phospholipases are also included as lipases.

Now, the method for causing the reaction of the present invention will be described below. The immobilized lipase is placed in the lipase reaction zones 6 provided with agitating means and kept fluidized by agitating and countercurrent flow and, at the same time, the oily substrate is supplied via the inlet 7 for the oily substrate and water-soluble substrate via the inlet 3 for the water-soluble substrate. As a result, the two substrates are brought into contact with the lipase and the water-soluble product is obtained via the outlet 9 for recovery of the water-soluble product and the oily product via the outlet 1 for the oily product-containing liquid. Let us assume that a high acid value oil is supplied as an oily substrate and glycerol as a water-soluble substrate. When the unaltered glycerol containing water is removed at a speed substantially equal to the feed rate of glycerol, a mixture of monoglyceride and triglyceride issues via the outlet for the oily product. Since the unaltered glycerol contains the water which is generated during the synthesis of glyceride, it is subjected to vacuum distillation for expulsion of the water. The residue of the vacuum distillation is used as a water-soluble substrate. As demonstrated in one working example, an oil is supplied as an oily substrate and water as a water-soluble substrate. When the water-soluble product is collected at a speed substantially equal to the feed rate of the water-soluble substrate, a mixture of a fatty acid and glyceride issues via the outlet for the oily product. When the water-soluble substrate is supplied at a rate lower than the feed rate of the oily substrate, continuous concentration of glycerin as the water-soluble product can be realized. To determine the highest possible concentration in which the glycerin is recovered, an experiment of the addition of glycerin has been made. The results of this experiment indicate that virtually no change is observed in the ratio of hydrolysis of oil even when the concentration of the recovered glycerin is increased to the range of 30 to 50%. Further it is realized that the concentration of glycerin is possible by repetitively using the water-soluble product as a water-soluble substrate for a long time. In the above case the ratio of hydrolysis of the oil is increased by increasing the feed rate of the aqueous phase (water-soluble substrate) to about 30 times that of the oil phase (oily substrate). And when the aqueous phase is repetitively used for a long time, the otherwise inevitable deterioration of the color tone of the oily product can be precluded by divesting the aqueous phase of impurities as with activated carbon.

The immobilizing carrier for the lipase of the present invention is desired to be of a type not easily worn because the immobilized lipase forms a fluidized bed and is agitated. The immobilization of the lipase can be carried out by any of the conventional methods such as the carrier immobilization method and the entrapping method which have been available for the immobilization of enzymes. Particularly desirable for the present invention is the immobilized lipase which has the enzyme immobilized in a fine hydrophobic carrier possessing particle diameters in the range of 0.02 to 0.3 mm and an anion-exchange group binding no lipase molecules on the carrrier. The term "hydrophobic carrier" as used herein refers to a carrier in the form of a macroporous ion-exchange resin. An amphiphilic carrier is obtained by introducing the anion-exchange group in the largest possible amount into the hydrophobic carrier mentioned above. For use in the method of the present invention, the amphiphilic carrier is desired to be of such nature that it will gain in specific gravity and sink in the upper-layer liquid (oily substance) after it has adsorbed the lower-layer liquid (water-soluble substance) of large specific gravity, whereas it will lose in specific gravity and float in the lower-layer liquid (water-soluble substance) after it has adsorbed the upper-layer liquid (oily substance). Generally, numerous species of anion-exchange resins exhibit the nature of an amphiphilic carrier. Any of these anion-exchange resins can be used for the present invention so long as it possesses the nature mentioned above. As concrete examples of the anion-exchange resin, such proprietary commodities as Dowex MWA-1 and Dowex 66 (Dow Chemical Company), Amberlite IRA 93 (Rohm and Haas Company), Diaion HPA 25 (Mitsubishi Chemical Industries, Ltd.), and Lewatit MP 64 (Bayer AG) may be mentioned. The anion-exchange resin is desired to possess particle diameters in the range of 0.02 to 0.3 mm. The immobilization of a lipase with the anion-exchange resin is attained by causing a solution containing an amount of lipase which is less than the number of atoms equal to one-thousandth of the ion-exchange capacity of the anion-exchange resin to come into contact with the anion-exchange resin.

For the immobilization of the lipase to be obtained with greater fastness, the immobilized lipase is further treated with such a polyfunctional reagent as glutaraldehyde, for example. Since this polyfunctional reagent produces an undesirable effect in food, the immobilized lipase treated therewith for the purpose mentioned above is desired to be thoroughly deprived of the excess polyfunctional reagent as with a reducing agent and then washed amply with water.

This invention characteristically aims to provide a method for continuous reaction which enables the reaction between the oily substrate and the water-soluble substrate and the separation of the oily product from the water-soluble product to proceed simultaneously. For the oily substrate and the water-soluble substrate to react with each other in such a manner as to alleviate the resistance offered by the immobilized lipase to the external diffusion, it is necessary that the speed of motion of the two substances on the surface of the immobilized lipase should be sufficiently high. For this purpose, the immobilized lipase, the oily substrate, and the water-soluble substrate must be agitated. When this agitation is continued unduly long, however, the oily substrate and the water-soluble substrate are transformed into an emulsion and the particles of this emulsion enter the pores of the immobilized lipase only with difficulty and, as a result, the resistance to internal diffusion is increased. Thus, the emulsion produced by the agitation must be broken up into an oily substrate in the form of a continuous phase. To fulfill this necessity, the lipase reaction zones 6 provided with agitating means and the separation zones 5 are alternately disposed in the vertical direction in the reaction region so that the fine emulsion possibly produced by the agitation will be broken up in the separation zones to such an extent as to facilitate the oil-water separation and ensure supply of the substrate in the form of a continuous phase to the subsequent lipase reaction zones. The seive plates 11 separating the separation zones 5 and the lipase reaction zones 6 are desired to be made of metal. For the recovery of the oily product and the water-soluble product, the reaction vessel is provided at the upper and lower ends thereof respectively with separation regions 2 and 8. By providing these separation regions each with emulsion breaking means provided with a portion packed with glass bead for example, the products which have undergone substantially complete oil-water separation are obtained. The oil-water separation proceeds with the breakage of the emulsion particles. This breakage of the emulsion proceeds with creaming, cohesion, and union. Since the speed of this oil-water separation more often than not is governed by the Stokes' law, the acceleration of the oil-water separation may be possibly obtained by increasing the diameter of the emulsion particles, increasing the difference of density between the oil and the water, lowering the viscosity of the dispersion medium, or heightening the gravitational velocity by exertion of centrifugal force, for example.

The mass transfer of the substrates and the corresponding products relative to the immobilized lipase can be divided into internal diffusion and external diffusion. The transfer of the substrates toward the enzyme molecules immobilized inside the immobilizing carrier and the transfer of the products produced by the enzyme molecules to the exterior of the immobilizing carrier make up the internal diffusion. When the fineness of the immobilizing carrier is increased, the distance of transfer is shortened and the impact of the resistance to the internal diffusion alleviated. The transfer of the substrates en route to the surface of the immobilizing carrier and transfer of the corresponding products away from the surface of the immobilizing carrier make up what is called the external diffusion. Where the immobilized lipase carrier is caused to form a fluidized bed as contemplated by the present invention, the floating speed of the immobilized lipase carrier in the reaction solution is increased, the transfer speed of the reaction solution relative to the surface of the immobilizing carrier increased, and the impact of the external diffusion resistance alleviated in proportion as the fineness of the immobilizing carrier is enhanced If the immobilizing carrier has particle diameters of not more than 0.02 mm, however, the reticular structure of the sieve plates precludes the leakage of the carrier particles only with difficulty. In this case, it is also difficult to keep the state of fluidization of the carrier particles within a fixed range by virtue of the difference of specific gravity between the two substrates. It is the nature of the immobilized lipase to adhere to the wall of the reaction apparatus or mutually cohere by adsorption to give rise to coarse masses If the immobilizing carrier has particle diameters exceeding 0.3 mm, said adverse phenomena peculiar to any fine powder more than offset the effects manifested in the improvement of mass transfer.

For the immobilizing carrier to offer a sufficient surface for entrapping the enzyme, it is required to possess a porous texture. The pores of the immobilizing carrier have diameters approximately in the range of 10 to 100 times ($10^2$ ↑ to $10^4$ ↑) the diameter of the enzyme molecules. When the carrier has sufficient fineness, the pores formed therein have small depth sufficient to permit easy immobilization of the enzyme. Consequently, the efficiency of immobilization is enhanced.

Moreover, since the present invention uses the immobilized lipase beads in which lipase molecules and anion-exchange groups coexist, a fatty acid possibly occurring in the reaction solution does not lower the pH value in microenvironment of the enzyme. Thus, the reaction is allowed to proceed even in the presence of a higher concentration of fatty acid. Further, since the enzyme molecules are hydrophobically or ionically linked in a multipoint pattern to the hydrophobic carrier, the immobilized lipase is enabled to offer ample resistance to chemically degenerating substances and prevent leakage of enzyme over a long period of continued use.

EXAMPLE 1

The lipase produced by *Pseudomonas fluorescens* biotype I-No. 1021 (Bikoken Deposit FERM-P No. 5495 dated Apr. 22, 1980; Budapest Treaty Deposit No. FERM BP-494 dated Mar. 1, 1984) was obtained from the broth, concentrated, and treated with acetone to prepare a partly refined product, i.e. a lipase possessing a specific activity of 504 units/mg of protein. This lipase was adsorbed on a carrier (product of Dow Chemical Company and marketed under tradename designation of "Dowex MWA-1") at an amount of 1,185 units of lipase per g of carrier. The composite of the carrier and the adsorbed lipase was treated with glutaraldehyde to strengthen the linkage, washed with water, and then dried by being suction filtered over a glass filter.

Then, a reaction apparatus constructed as illustrated in the diagram was prepared. In the apparatus, lipase reaction zones 6 and separation zones 5 were partitioned each with a stainless steel sieve plate 11 (160 mesh). This reaction apparatus was encircled with a jacket (not shown) so as to be maintained at a fixed temperature of 60° C. It was provided at the upper and lower ends thereof respectively with conical separation regions 2 and 8, between the upper separation region 2 and the uppermost reaction zone with an inlet for introducing a water-soluble substrate, at the apex of the separation region 2 with an outlet 1 for issuing of an oily product, and between the lower separation region 8 and the lowermost reaction zone with an inlet 7 for introducing an oily substrate at the bottom of the separation region 8 with an outlet 9 for issuing of water soluble product. Inside the apparatus, the separation zones 5 and the reaction zones 6 were alternately disposed in the vertical direction. These zones are 100 mm in diameter and 30 to 31 mm in height each. The reaction zones were each charged with 35 g (in dry weight) of the aforementioned immobilized lipase. They were each provided with a paddle type agitating blade 4 inclined at an angle of 45 degrees and adapted to produce 10 complete rotations per 77 seconds so as to keep the immobilized lipase beads floating. A stirring shaft 10 was covered with a stirring shaft cover 12 in the portions outside the reaction zones.

At first, water and olive oil were each supplied at a flow rate of about 10 ml/hour to the reaction apparatus, with the agitating blades kept idle and the outlet 9 for release of water-soluble product kept closed. After the reaction vessel was filled to capacity with the water and olive oil, the agitating blades were set rotating and the supply of water at a rate of 2.5 ml per hour and the supply of olive oil at a rate of 5 ml per hour were started. When the recovery volume of the water-soluble product via the lower end was adjusted to 2.5 ml per hour, the oily product was obtained via the upper end at a rate of about 5 ml per hour.

After the elapse of 525 hours following the start of the reaction, the reaction was continued at a fixed temperature of 60° C. After the elapse of 762 hours following the start of the reaction, the feed rate of water was kept at 0.8 ml/hour and that of olive oil at 1.5 ml/hour until after the elapse of 1,201 hours. Then after the elapse of 1,550 hours following the start of the reaction, the reaction was continued again with the feed rate of water fixed at 2.5 ml/hr and that of olive oil at 5.0 ml/hr. The changes in the olive oil hydrolysis ratio and the glycerin concentration during the course of this operation were as shown in Table 1. The ratio of hydrolysis was determined by the method described in Example 2 and the glycerin concentration by the colorimetry using periodic acid. Though the first sign of physical breakage of the immobilized lipase was observed after the reaction lasted for about one month and a half, the possible leakage of immobilizing carrier was substantially completely prevented owing to the amphiphilicity of the carrier.

TABLE 1

| Reaction time (hrs) | 525.2 | 698.2 | 762.0 | 1032.2 | 1141.1 | 1201.0 | 1555.0 | 1842.3 |
| --- | --- | --- | --- | --- | --- | --- | --- | --- |
| Feed rate of olive oil (ml/hr) | 5.0 | → | 1.5 | → | → | → | 5.0 | → |
| Hydrolysis rate of oily product (%) | 77.5 | 79.1 | 79.4 | 83.5 | 83.0 | 82.7 | 84.9 | 71.7 |
| Feed rate of water phase (ml/hr) | 2.5 | → | 0.8 | → | → | → | 2.5 | → |
| Glycerol concentration in water phase (mg/ml) | 108.7 | | 110.5 | | | 124.3 | 147.3 | |

It is clearly noted from Table 1 that the decline of the hydrolysis ratio of oil was less than 10% even after about two months' continued operation at 60° C. and that the glycerol concentration was increased by decreasing the feed rate of the water layer to half of that of the oil layer.

With the feed rate of the oil phase fixed and that of the water phase increased from 0.8 ml/hr to 24 ml/hr, the water-soluble product was circulated to the reaction apparatus as a water-soluble substrate. The results of this operation were as shown in Table 2.

TABLE 2

| Reaction time (hrs) | 762 | 1032 | 1141 | 1201 | 1219 | 1289 | 1312 | 1344 | 1438 |
|---|---|---|---|---|---|---|---|---|---|
| Feed rate of oily phase (ml/hr) | 1.5 | → | → | → | → | → | → | → | |
| Feed rate of aqueous layer (ml/hr) | 0.8 | → | → | → | 24 | → | → | → | → |
| Resolution ratio of oil (%) | 7.94 | 83.5 | 83.0 | 82.7 | | 84.0 | 85.4 | 86.6 | 86.7 |

It is clearly noted from this table that the hydrolysis ratio of oil was improved when the feed rate of the aqueous phase was increased to 30 times the original feed rate. This improvement may be logically explained by a supposition that the impact of the external diffusion resistance was eliminated by the increased feed rate of the aqueous phase.

After 2057.6 hours' operation, the reaction was continued in the absence of agitation to study the influence of agitation upon the reaction. The results were as shown in Table 3.

TABLE 3

| Reaction time (hrs) | 1792.5 | 1816.5 | 1842.3 | 2057.6 | 2154.9 | 2178.4 | 2205.7 | 2231.4 | 2304.5 |
|---|---|---|---|---|---|---|---|---|---|
| Resolution ratio of oil (%) | 71.9 | 72.3 | 71.1 | | 63.1 | 62.3 | 60.8 | 61.3 | 63.0 |
| Presence of agitation | yes | → | → | no | → | → | → | → | → |

It is clearly noted from this table that the hydrolysis ratio of oil was lower in the absence of agitation. The results indicate that the agitation eliminated the impact of the external diffusion resistance and, at the same time, promoted the oil-water separation in the reaction zones packed with the immobilized lipase. The immobilized lipase in the second layer was sampled after 2304.5 hours' (about 96 days') operation, and the sample was washed with a 2 : 1 mixed solution of benzene-acetone and tested for activity per unit weight. The results were as shown in Table 4.

TABLE 4

| Immobilized lipase activity before the reaction | 71.9 units/g |
|---|---|
| Immobilized lipase activity after 2304.5 hours' reaction | 50.0 units/g |

It is clearly noted from this table that the residual activity of the immobilized lipase was about 70%.

EXAMPLE 2

An ion-exchange resin (total exchange capacity 4.2 meg/g min.) (product of Dow Chemical Company and marketed under tradename designation of "Dowex MWA-1) was pulverized in a mortar and separated by sieves to produce carriers of different particle sizes shown in Table 5. Of these carriers, 2-g portions were taken as specimens and subjected to the following treatment. First, the specimens was each mixed with 6 ml of the same lipase solution (5,640 units) as used in Example 1 and shaken overnight at 8° C. The resultant mixture and 0.32 ml of a 25% glutaraldehyde solution added thereto were shaken at 8° C. for 10 minutes. Subsequently, the resultant mixture and 0.8 ml of a 20% sodium hydrogen sulfite solution added thereto were shaken at 8° C. for 10 minutes, washed thoroughly with water, and dried on a glass filter, to produce a preparation having the lipase immobilized on a fine powder of Dowex MWA-1 as a carrier. The lipase purified to a specific activity 2,000 to 2,500 units/mg of protein, on analysis by the SDS electrophoresis, was found to possess a molecular weight of 120,000. The mol number of the 5,640 units of the lipase was as follows.

$$\text{Mol number of lipase} = (5{,}640/2{,}500) \times 10^{-3}/(1.2 \times 10^5)$$
$$= 2 \times 10^{-8} \text{ (mols)}$$

The ratio of this number to the exchange capacity of the Dowex MWA-1 is found as follows.

$$4.2 \times 2 \times 10^{-3}/(2 \times 10^{-8}) = 4.2 \times 10^5$$

This means that in the immobilized lipase, $4.2 \times 10^5$ anion-exchange groups per molecule of the lipase was present on the hydrophobic carrier.

Then, the immobilized lipase was tested to determine the ratio of immobilization of the lipase on the carrier. First, the lipase activity of the washings obtained by the aforementioned immobilized lipase was washed with water was tested by the modified Nord et al.'s method [Nichinoka, Vol. 36, page 860 (1962)]. The activity of the lipase adsorbed on the carrier was found by deducting the found value from the total activity, 6,540 units and the ratio of immobilization was calculated. Then, the immobilized lipase was tested for activity by the following method. In a conical flask having an inner volume of 50 ml, a reaction solution consisting of 2 g of olive oil, 0.2 ml of a 0.1 M phosphate buffer (pH 7), and the immobilized lipase (0.01-0.1 g) was shaken for reaction The reaction was stopped with 10 ml of a methanol-chloroform mixture (2:1). The resultant solution mixture was tested for the concentration of the produced fatty acid by titration with a liquid produced by dissolving 0.05 ml of NaOH in 95% methanol. In any case, one unit of lipase was fixed at an amount which liberated 1 micro mol of acid per minute at 60° C. at pH 7. The results were as shown in Table 5.

TABLE 5

| Particle diameter (mm) | Activity of washings (unit) | Ratio of immobilization (%) | Activity of immobilized lipase (unit/2 g) |
|---|---|---|---|
| 0.02-0.037 | 3.1 | 99.8 | 66.4 |
| 0.038-0.177 | 6.3 | 99.9 | 69.0 |
| 0.178-0.300 | 391.0 | 93.1 | 31.8 |
| 0.301-0.840 | 483.0 | 91.4 | 25.4 |
| 0.841-1.68 | 756.2 | 86.6 | 15.0 |

It is clearly noted from this table that the ratio of immobilization and the activity of the immobilized lipase were both enhanced as the fineness of the carrier powder increased.

Then, the ratio of hydrolysis was determined. In a conical flask having an inner volume of 100 ml and furnished with a silicon stopper, 1 g of live oil, 1 g of water, and the immobilized lipase (0.15-0.5 g) were shaken for reaction at 60° C. After the reaction, the immobilized lipase was washed with a 1:1 ethanol/benzene mixture on a filter paper No. 2 to extract the hydrolyzate. The extract was tested for acid value and saponification value. The ratio of hydrolysis was calculated based on the ratio of the two values mentioned above. The results were as shown in Table 6. The reaction involved in this experiment may well be regarded as faithfully representing the reaction in the fluidized bed using a large amount of the immobilized lipase.

TABLE 6

| Particle diameter | Ratio of hydrolysis Reaction time | | |
|---|---|---|---|
| | 23.15 hr | 120 hr | 22 hr |
| | Amount of enzyme | | |
| | 0.15 g | 0.15 g | 0.75 g |
| 0.02 mm-0.037 mm | 63.4% | 91.2% | 89.8% |
| 0.038-0.177 | 48.7 | 78.2 | 90.8 |
| 0.178-0.300 | 36.7 | 61.5 | 85.2 |
| 0.301-0.840 | 53.9 | 76.0 | 86.6 |
| 0.841-1.68 | 59.4 | 81.5 | 88.7 |

Generally when immobilized lipase beads of a small particle diameter are used in a large volume, they are reliable to adhere to the inner wall of the reaction vessel or cohere into large lumps. By this physical phenomenon, the hydrolysis effected by the lipase is impaired. When the particle diameter exceeds 0.3 mm, the aforementioned physical phenomena bring about a significant influence. It is clearly noted from Table 6 that when the particle diameter was not more than 0.3 mm, the increase of the activity of the individual immobilized lipase due to the size reduction more than offsets the decrease of the ratio of hydrolysis caused by the aforementioned physical phenomena due to the size reduction and that the ratio of hydrolysis increased in proportion as the fineness of the carrier powder increased. The data indicate that the immobilized lipase retained sufficient ratio of hydrolysis when the particle diameter was in the range of 0.02 to 0.3 mm.

EXAMPLE 3

An ion-exchange resin (produced by Dow Chemical Company and marketed under tradename designation of "Dowex MWA-1") was pulverized and separated to obtain two species of carrier, one possessing a particle diameter not exceeding 0.3 mm and the other a particle diameter exceeding 0.3 mm. Of these carriers, 2-g portions taken as specimens were each washed with water. The washed specimen and 3 ml of the same lipase liquid (2,820 units) as used in Example 2 were shaken overnight at 8° C. The resultant mixture and 3 ml of water and 0.32 ml of a 25% glutaraldehyde solution added thereto were processed in the same manner as in Example 2, to obtain an immobilized lipase on Dowex MWA-1. The immobilized lipase samples thus obtained were tested for activity of washings, ratio of immobilization, and activity of immobilized lipase by following the procedure of Example 2. The results were as shown in Table 7.

TABLE 7

| Particle diameter (mm) | Activity of washing (unit) | Ratio of immobilization (%) | Activity of immobilized lipase (unit/2 g) |
|---|---|---|---|
| 0.02-0.300 | 59.0 | 97.9 | 151.6 |
| 0.301-1.68 | 780.9 | 72.3 | 43.3 |

It is clearly noted from Table 7 that the carrier of greater fineness showed better results in ratio of immobilization and in immobilized lipase activity. Even when the volume of the lipase solution was decreased from 6 ml to 3 ml, the produced immobilized lipase exhibited high activity. Then, the immobilized lipase was tested for ratio of hydrolysis in the same manner as in Example 2. The results were as shown in Table 8.

TABLE 8

| Particle diameter | Ratio of hydrolysis Reaction time | |
|---|---|---|
| | 21.2 hr | 58 hr |
| | Amount of enzyme | |
| | 0.5 g | 0.5 g |
| 0.02 mm-0.30 mm | 81.8% | 96.3% |
| 0.301-1.68 (not pulverized) | 65.5 | 86.4 |

It is clearly noted from Table 8 that the carrier powder of greater fineness showed a higher ratio of hydrolysis.

We claim:

1. A method for continuous reaction of a water-soluble substrate and an oily substrate in the presence of fluidized immobilized lipase, which comprises:
    (a) providing a reaction vessel having (i) vertically maintained apart upper and lower conically-shaped separation regions, respectively, for separation of a water-soluble product and an oily product, (ii) a plurality of lipase reaction zones each containing immobilized lipase capable of being fluidized and containing therein agitating means and (iii) a plurality of intermediate separation zones for separation of an oily substance and a water-soluble substance, said lipase reaction zones and said intermediate separation zones being disposed alternately between said upper and lower conically-shaped separation regions, and boundaries between said lipase reaction zones and intermediate separation zones being pervious to liquid but impervious to said immobilized lipase;
    (b) feeding said water-soluble substrate into a lower part of the upper conically-shaped separation region and said oily substrate into an upper part of the lower conically-shaped separation region;
    (c) passing said water-soluble substrate and said oily substrate in counterflow contact through said lipase reaction zones and said intermediate separation zones whereby said immobilized lipase in a fluidized contact with said oily substrate and said water-soluble substrate state comes into mutual; and
    (d) recovering oily product-containing liquid from an upper part of said upper conically-shaped separation region and water-soluble product-containing liquid from a lower part of said lower conically-shaped separation region.

2. The method according to claim 1, wherein said oily substrate is fed at a flow rate higher than the flow rate at which said water-soluble substrate is fed.

3. The method according to claim 1, wherein said water-soluble product-containing liquid emanating from the lower separation region is supplied to the upper part of the uppermost lipase reaction zone.

4. The method according to claim 1, wherein said immobilized lipase comprises a lipase immobilized on a fine hydrophobic carrier possessing particle diameters in the range of 0.02 to 0.3 mm, and an anion-exchange residue deposited on said carrier.

5. The method according to claim 1, wherein said upper and lower separation regions each are partially packed with glass beads.

6. The method according to claim 1, wherein said oily substrate has a specific gravity less than that of water and is soluble in a non-polar solvent.

7. The method according to claim 6, wherein said oily substrate comprises oils, fats, waxes, phospholipids, esters, monoglycerides, diglycerides and fatty acids.

8. The method according to claim 1, wherein said water-soluble substrate is water, a water-soluble organic compound or an aqueous solution of an organic compound.

9. The method according to claim 4, wherein said carrier has a porous texture with pores having diameters of about 100 Å to 10,000 Å.

10. The method according to claim 1, wherein said separation zones and separation regions are maintained at a temperature in excess of 50° C.

11. The method according to claim 1, wherein said separation zones and lipase reaction zones are separated by sieve plates capable of precluding passage of immobilized lipase.

12. The method according to claim 1, wherein said lipase is an esterase.

13. The method according to claim 1, wherein said lipase is a phospholipase.

* * * * *